(12) United States Patent
Govindappa et al.

(10) Patent No.: US 8,975,041 B2
(45) Date of Patent: Mar. 10, 2015

(54) FUSION PROTEINS AND METHOD OF EXPRESSION THEREOF

(75) Inventors: Nagaraj Govindappa, Kodagikere (IN); Nandini Nataraj, Bangalore (IN); Sanjay Tiwari, Bangalore (IN); Partha Hazra, Bangalore (IN); Mukesh Babuappa Patale, Ausa (IN); Gokul Jothiraman, Hosur (IN); Kedarnath Sastry, Bangalore (IN)

(73) Assignee: Biocon Limited (IN)

( * ) Notice: Subject to any disclaimer, the term of this patent is extended or adjusted under 35 U.S.C. 154(b) by 338 days.

(21) Appl. No.: 13/395,292

(22) PCT Filed: Oct. 26, 2009

(86) PCT No.: PCT/IN2009/000603
§ 371 (c)(1),
(2), (4) Date: Mar. 9, 2012

(87) PCT Pub. No.: WO2011/030347
PCT Pub. Date: Mar. 17, 2011

(65) Prior Publication Data
US 2012/0231520 A1 Sep. 13, 2012

(30) Foreign Application Priority Data
Sep. 10, 2009 (IN) .......................... 2193/CHE/2009

(51) Int. Cl.
*C12N 9/20* (2006.01)
*C12N 9/64* (2006.01)
*C12N 9/76* (2006.01)
*C12P 21/06* (2006.01)

(52) U.S. Cl.
CPC .............. *C12N 9/20* (2013.01); *C07K 2319/00* (2013.01); *C12N 9/6424* (2013.01); *C12N 9/6427* (2013.01); *C12P 21/06* (2013.01)
USPC ........................................................ 435/69.7

(58) Field of Classification Search
CPC combination set(s) only.
See application file for complete search history.

(56) References Cited

U.S. PATENT DOCUMENTS 7,276,605 B2 10/2007 Muller et al.

FOREIGN PATENT DOCUMENTS

WO WO-97/00316 A1 1/1997

OTHER PUBLICATIONS

Vasquez, et al., Journal of Cellular Biochemistry, 1989, vol. 39, p. 265-276.
Nemoda, et al., Journal of Biological Chemistry, 2005, vol. 280, No. 33, p. 29645-29652.
Burgess, TL et al., The Journal of Cell Biology, 1987, vol. 105, pp. 659-668.
International Search Report and Written Opinion (mailed May 6, 2010) and International Preliminary Report on Patentability (mailed Sep. 1, 2011) for PCT/IN2009/000603; ISA/AU.

*Primary Examiner* — Sheridan Swope
(74) *Attorney, Agent, or Firm* — Schwegman Lundberg & Woessner, P.A.

(57) ABSTRACT

The present invention relates to novel Prolipase-Bovine trypsinogen (PLBTR) fusion proteins, the genes encoding them, and the production and uses thereof. More specifically, the present invention relates to methods of producing in optimal quantities PLBTR fusion proteins which comprise a heterologous polypeptide which is normally susceptible to autocatalytic activity. More particularly, the present invention relates to fusion proteins which comprise an heterologous polypeptide, such as a serine protease, fused to a lipase signal sequence, which can be expressed by recombinant host cells in desired amounts. The present invention further relates to polynucleotides encoding such fusion proteins, to expression vectors for expression of such fusion proteins, to host cells transformed with such polynucleotides/vectors, and to methods of generating such fusion proteins.

Figure 1:
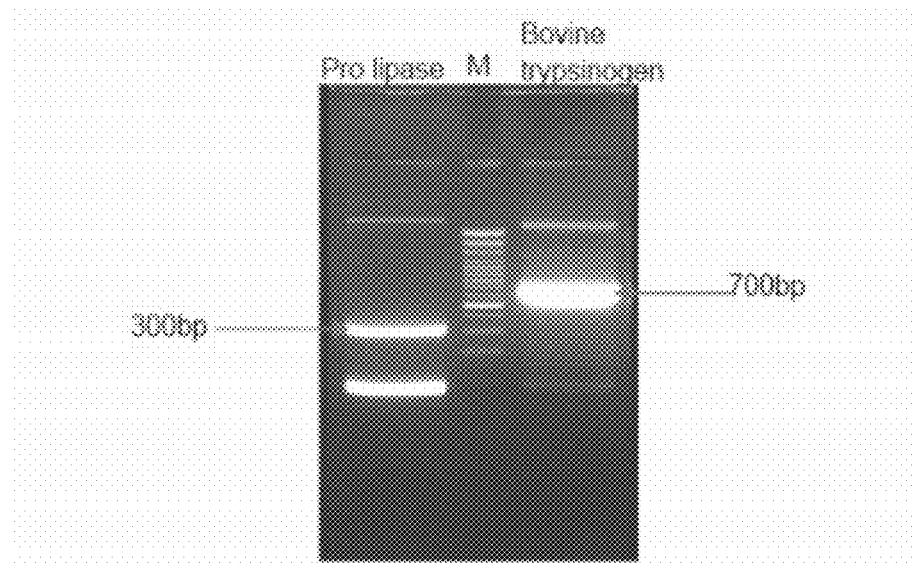

9 Claims, 10 Drawing Sheets
(6 of 10 Drawing Sheet(s) Filed in Color)

FUSION PROTEINS AND METHOD OF EXPRESSION THEREOF

CROSS-REFERENCE TO RELATED APPLICATIONS

This application is a 371 U.S. National Stage of International Application No. PCT/IN2009/000603, filed Oct. 26, 2009. This application claims priority to Indian Patent Application No. 02193/CHE/2009, filed Sep. 10, 2009. The disclosures of the above applications are incorporated herein by reference.

FIELD OF THE INVENTION

The present invention relates to novel Prolipase-Bovine trypsinogen (PLBTR) fusion proteins, the genes encoding them, and the production and uses thereof. More specifically, the present invention relates to methods of producing in optimal quantities PLBTR fusion proteins which comprise a heterologous polypeptide which is normally susceptible to autocatalytic activity. More particularly, the present invention relates to fusion proteins which comprise an heterologous polypeptide, such as a serine protease, fused to a lipase signal sequence, which can be expressed by recombinant host cells in desired amounts. The present invention further relates to polynucleotides encoding such fusion proteins, to expression vectors for expression of such fusion proteins, to host cells transformed with such polynucleotides/vectors, and to methods of generating such fusion proteins.

BACKGROUND AND PRIOR ART OF THE INVENTION

Trypsin is a highly valuable protease that has many industrial and biomedical applications. The growing demand for non-animal sources of trypsin with special properties has driven the interest to clone and express this protease in microorganisms. Reports about expression of recombinant trypsins show wide differences in the degree of success owing to difficulties associated with its expression and autocatalytic properties of the protein. The yeast *Pichia pastoris* appears to be the microbial host with the greatest potential for the production of trypsin.

Trypsin is a serine protease of ~25 kDa, secreted by acinar cells of pancreas as an inactive precursor—trypsinogen. An activation peptide of amino acids DDDDK precedes the mature trypsin in trypsinogen, which is cleaved by enterokinase, in the intestinal lumen. The activated trypsin will cleave the proteins at the carboxyl-terminal end of accessible Arginine (R) and Lysine (K) amino acid residues. Trypsin will not only digest any protein containing accessible R and K, but also acts on the accessible R and K of its own sequence and degrades itself (autocatalytic activity). Hence it is a very big challenge to produce recombinant trypsin in microbial or mammalian systems. Moreover expression levels are very low. To overcome this problem, the inventors of the present invention have fused 97 amino acid *Rhizopus oryzae* lipase signal sequence to Bovine Trypsinogen and expressed it in *Pichia pastoris*. The presence of prolipase sequence stabilizes the expression of trypsinogen and appeared to prevent activation in vivo.

Prolipase acts as an N-terminal extension of lipase, distinct from the signal sequence which is necessary for the transport of the protein into or through the membrane, or for its secretion into the extracellular medium. The 69 amino acid propeptide region of the *Rhizopus oryzae* lipase immediately follows the 26-amino acid signal sequence. Previous studies have shown that a mutation (C56 to S) in the prolipase region slows down the folding of lipase (Beer H. D., Wohlfahrt G., Schmid R. D., McCarthy J. E. G., Biochem. J. 319:351-359, 1996). The replacement of proregion of native bovine trypsinogen with prolipase region from *Rhizopus oryzae* lipase, surprisingly improved the stability and the yield of the recombinant bovine trypsinogen.

The known state of art fails to provide a generally applicable method of producing in a satisfactorily/optimally purifiable form of heterologous fusion polypeptides, expressed in a suitable host cell.

There is thus a widely recognized need for, and it would be highly advantageous to have, a method devoid of the above limitation.

The modified novel Prolipase-Bovine trypsinogen fusion protein of the present invention, overcomes the above-discussed and numerous other disadvantages and deficiencies of the prior art.

OBJECTIVE OF THE INVENTION

The main objective of the present invention is to obtain fusion polypeptides comprising at least one serine protease fused to a lipase signal sequence.

Another main objective of the present invention is to obtain a method of expressing a fusion polypeptide.

Yet another main objective of the present invention is to obtain a vector comprising sequences as described above.

Still another main objective of the present invention is to obtain a transformed cell comprising sequence as described above in an expressible form.

STATEMENT OF THE INVENTION

Accordingly, the present invention relates to a fusion polypeptide comprising at least one serine protease fused to a lipase signal sequence, said fusion polypeptide being expressed in a methyloptropic yeast wherein said fusion polypeptide has an amino acid sequence at least 80 percent homologous to SEQ ID NO: 2; a fusion polypeptide comprising at least one serine protease fused to a lipase signal sequence, said fusion polypeptide being expressed in a methyloptropic yeast wherein said fusion polypeptide has nucleotide sequence at least 80 percent homologous to SEQ ID NO: 1; a method of expressing a fusion polypeptide comprising at least one serine protease fused to a lipase signal sequence produced from a methylotrophic yeast said fusion polypeptide having a nucleotide sequence that is at least 80% homologous to the nucleotide sequence represented by SEQ ID NO: 1 or amino acid sequence represented by SEQ ID NO: 2; a vector comprising sequence as described above; and a transformed cell comprising sequence as described above in an expressible form.

BRIEF DESCRIPTION OF THE ACCOMPANYING FIGURES

The patent or application file contains at least one drawing executed in color. Copies of this patent with color drawings will be provided by the Patent and Trademark Office upon request and payment of the necessary fee.

FIG. 1: PCR amplified products of Prolipase and Bovine Trypsinogen coding sequences.

Figure 2:
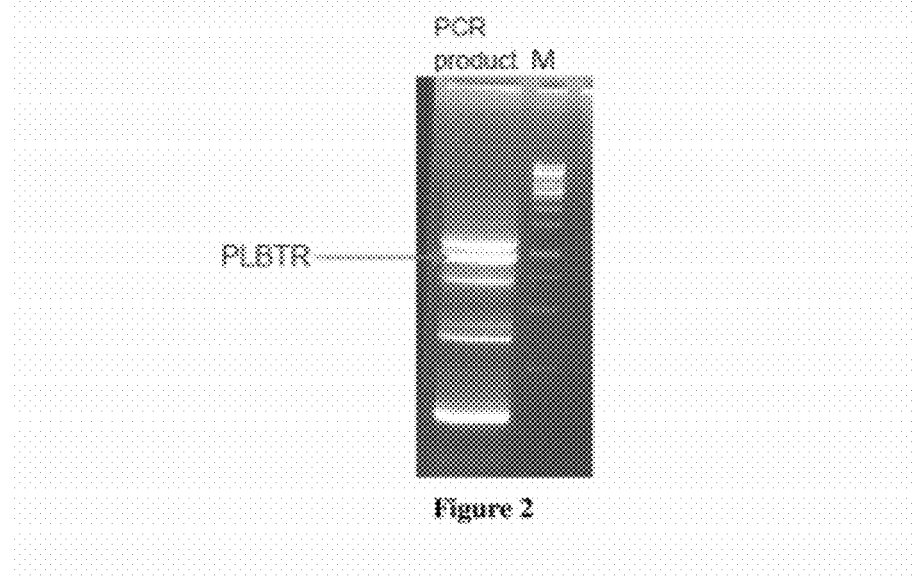

FIG. 2: Amplified PCR product of fused PLBTR.

Figure 3:
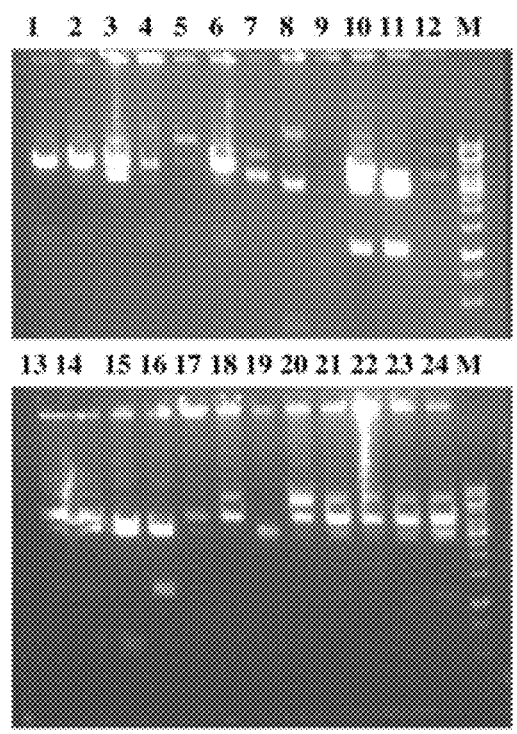

FIG. 3: The PLBTR band shown in FIG. 2 (arrow head) is cloned into pTZ57R vector and transformed to *E. coli* cells.

The individual colonies obtained are selected. Plasmid DNA is isolated from each of these colonies and digested using restriction enzymes XbaI and BamHI which are in the flanking region of the vector to identify the clones containing the correct insert. Lanes labelled 1 to 12 (top gel) and 13 to 24 (bottom gel) correspond to the different clones/colonies. The lanes named 'M' are the DNA molecular weight marker. Correct insert is released from clone/lane nos. 10, 11 and 16. Clone #10 is selected for further studies.

Figure 4:
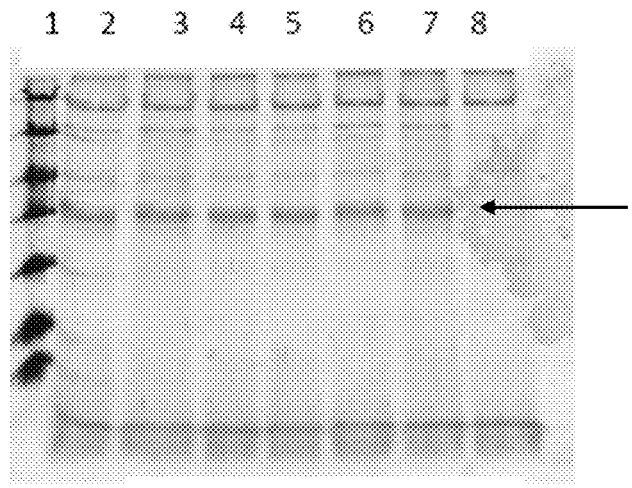
Figure 4:
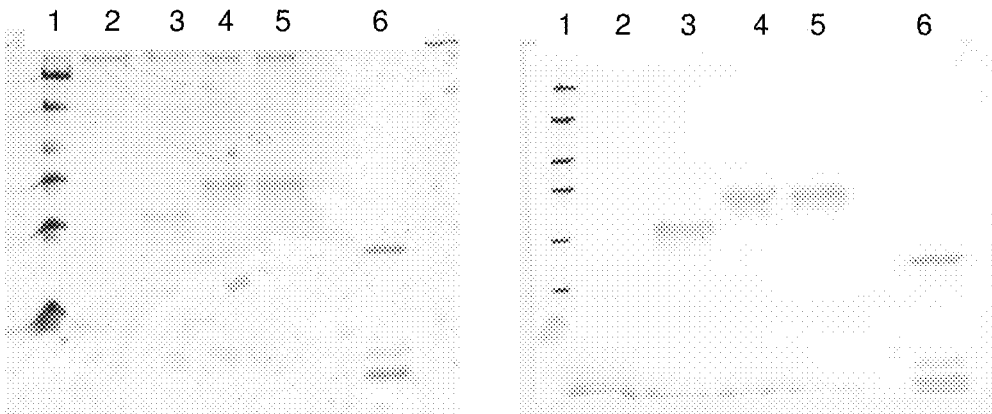
Figure 4:
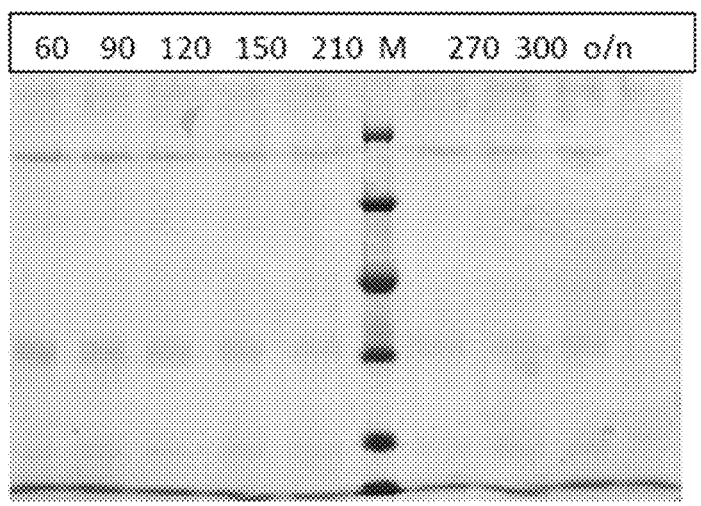

FIG. 4A: The Trypsinogen producing *P. pastoris* clones are developed. Six clones are selected for induction studies using shake flask. Lane 1 is a protein molecular weight marker, lanes 2-7 are six individual *P. pastoris* clones producing trypsinogen (all are secreting trypsinogen as shown by the arrow head), and lane 8 is a *P. pastoris* GS115 control as there is no trypsinogen band observed.

FIG. 4B: Both the pictures shown in the left and the right panel are replicates. The left panel is SDS-PAGE and the right panel is the Western blot of the same gel developed using trypsin antibodies. Lane 1 is a protein molecular weight marker, lane 2 is a *P. pastoris* parent strain, lane 3 is Bovine trypsinogen, lanes 4&5 are prolipase bovine trypsinogen, and lane 6 is Standard trypsin obtained from Sigma-Aldrich. The western blot developed with a specific antibody confirms that the protein secreted is indeed trypsinogen only.

FIG. 4C: SDS-PAGE showing the activated PLBTR. Lane 1 is a protein molecular weight marker, lane 2 is PLBTR CLONE#1, lane 3 is PLBTR CLONE#2, lane 4 is PLBTR CLONE#3, lane 5 is PLBTR CLONE#4, lane 6 is PLBTR CLONE#5, lane 7 is PLBTR CLONE#6, and lane 8 is a GS115 parent strain.

Figure 5:
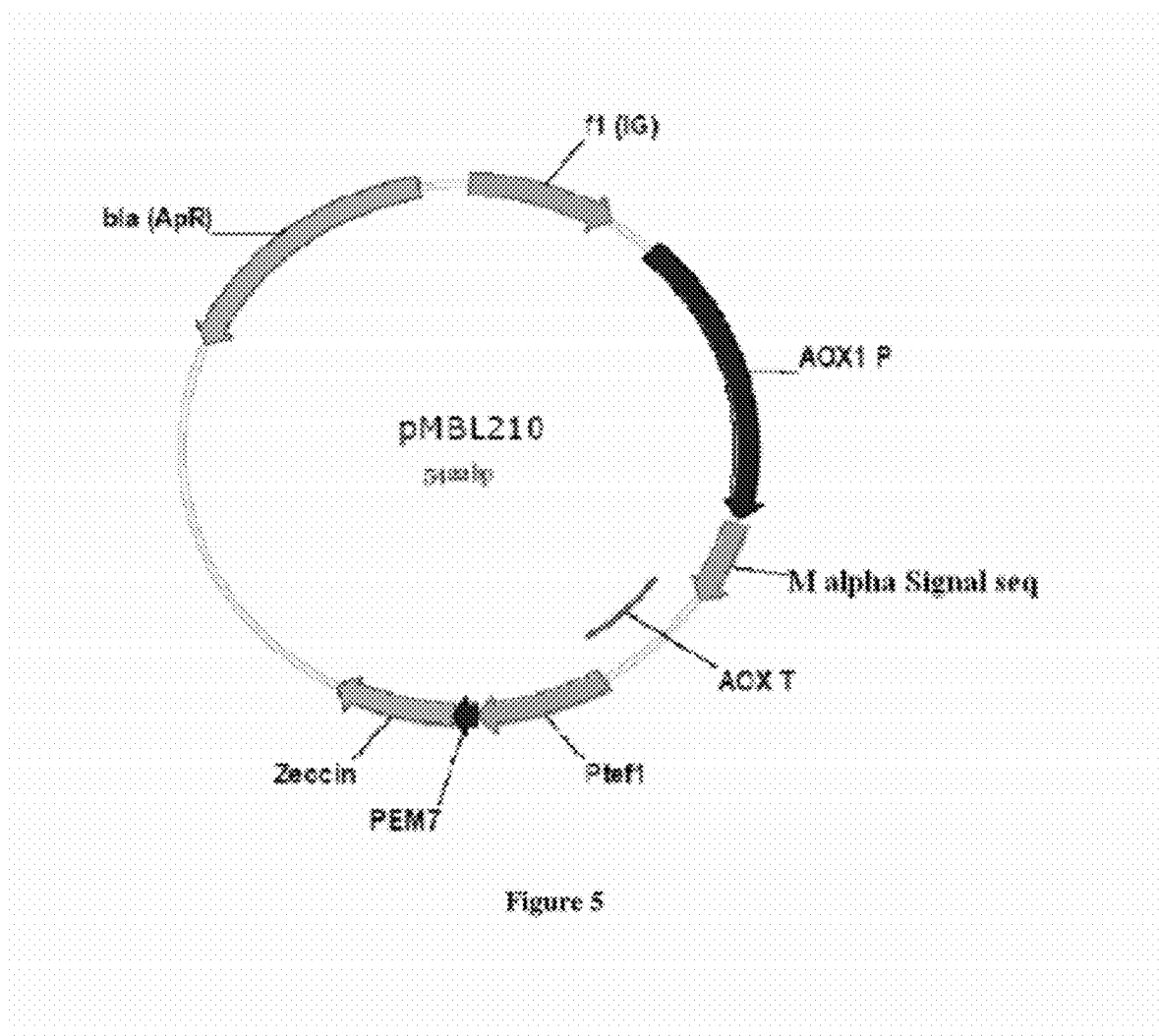

FIG. 5: pMBL210 Vector details

Figure 6:
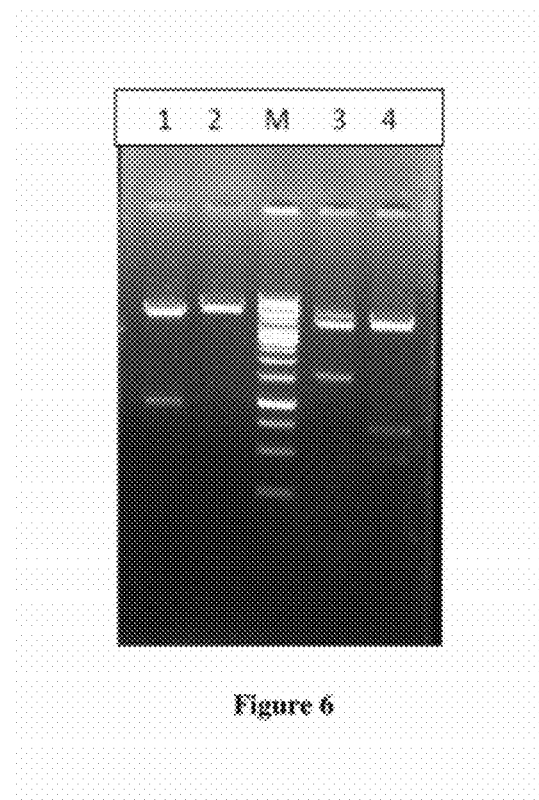

FIG. 6: Restriction enzyme profile of CPLBTR/pMBL210 clone #3.

Lane 1: CPLBTR/pMBL210 Clone #3 with EcoRI+XhoI (5400 bps+1030 bps)

Lane 2: CPLBTR/pMBL210 Clone #3 with Sad (linearize, 6426 bps)

Lane M: Gene ruler 1 Kb DNA ladder.

Lane 3: CPLBTR/pMBL210 Clone #3 with NdeI+KpnI (4781 bps+1645 bps).

Lane 4: CPLBTR/pMBL210 Clone #3 with XbaI (5104 bps+806 bps+516 bps)

Figure 7:
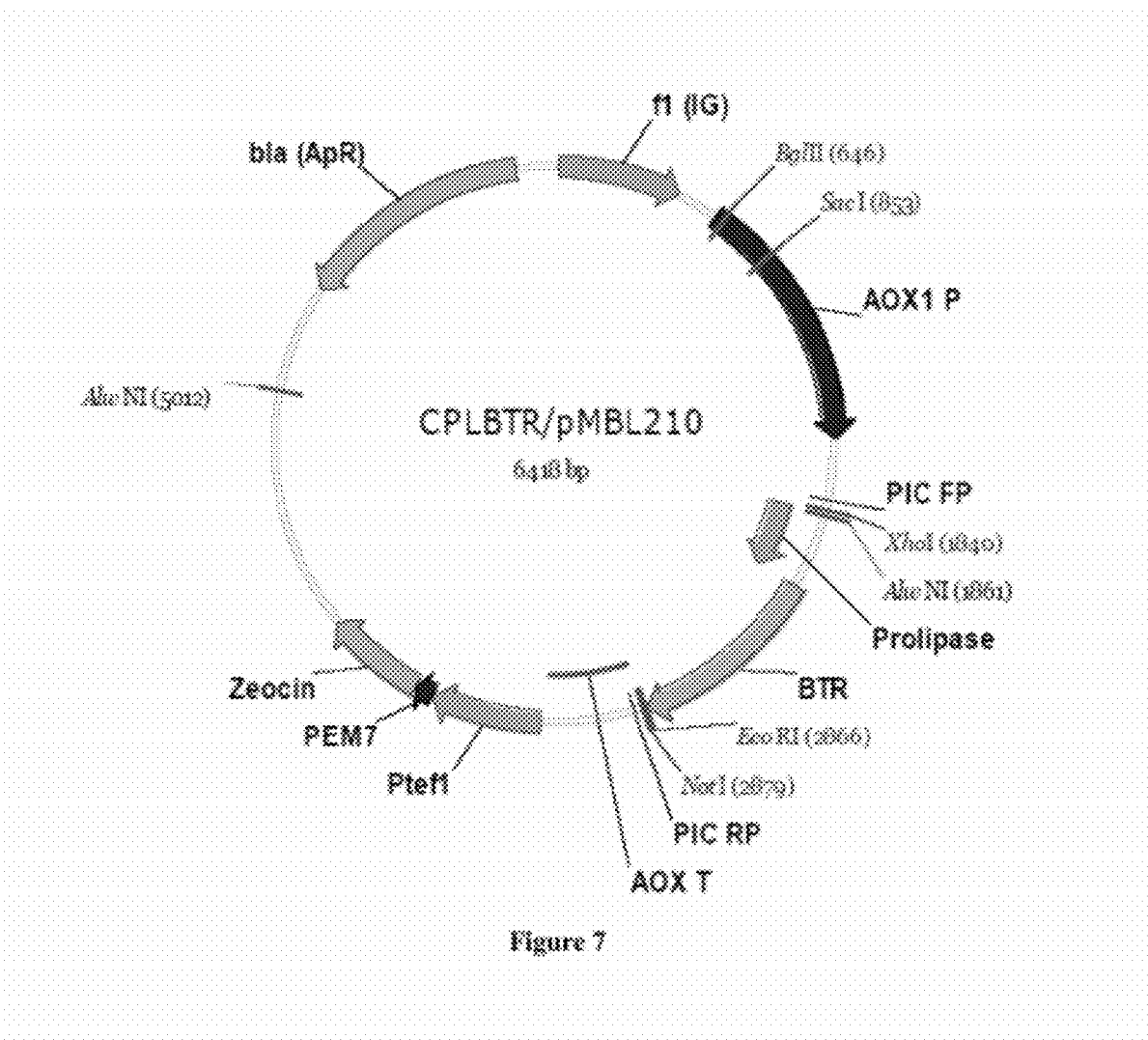

FIG. 7: CPLBTR/pMBL210 vector details.

Figure 8:
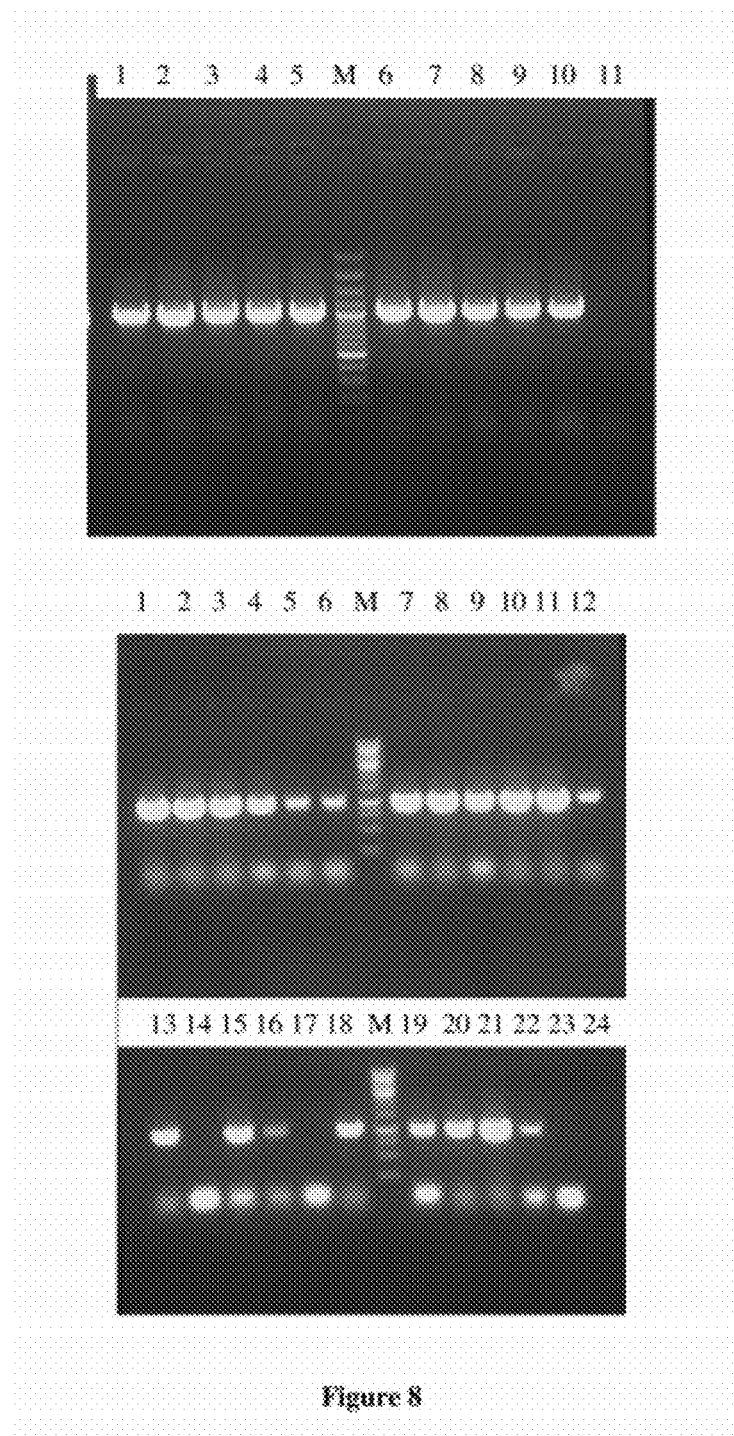

FIG. 8: PCR confirmation of Gene integration into the genome of all the Zeocin resistant clones.

Lane 1-16: 9453 Zeo$_{2500}$ Resistant colonies.

Lane 17: 9453 Host (Negative Control).

Lane 18: Positive Control (CPLBTR/pMBL210 Plasmid).

Lane M: 1 Kb DNA ladder.

Lane 19-22: 9452 Zeo$_{2500}$ Resistant colonies.

Lane 23: 9452 Host (Negative Control).

FIG. 9:

A, Analysis of prolipase bovine trypsinogen obtained from several 9450 clones.

B, Analysis of prolipase bovine trypsinogen obtained from several 9453 clones.

C, SDS PAGE and western blot using Trypsinogen antibody

FIG. 9A: Lane M=Protein molecular wt. marker

Lane 1=PLBTR clone #1

Lane 2=CPLBTR 9450 clone#1

Lane 3=CPLBTR 9450 clone#2

Lane 4=CPLBTR 9450 clone#3

Lane 5=CPLBTR 9450 clone#4

Lane 6=CPLBTR 9450 clone#5

Lane 7=CPLBTR 9450 clone#6

Lane 8=CPLBTR 9450 clone #7

Lane 9=CPLBTR 9450 clone #8

FIG. 9B: Lane M=Protein molecular wt. marker

Lane 1=PLBTR clone #1

Lane 2=CPLBTR 9453 clone#1

Lane 3=CPLBTR 9453 clone#2

Lane 4=CPLBTR 9453 clone#3

Lane 5=CPLBTR 9453 clone#4

Lane 6=CPLBTR 9453 clone#5

Lane 7=CPLBTR 9453 clone#6

Lane 8=CPLBTR 9453 clone #7

Lane 9=CPLBTR 9453 clone #8

FIG. 9C: Lane M: Protein molecular weight marker

Lane 1: Standard trypsin

Lane 2: Host control

Lane 3: PLBTR clone #1

Lane 4: CPLBTR 9450#1

Lane 5: CPLBTR 9453#6

Figure 10:
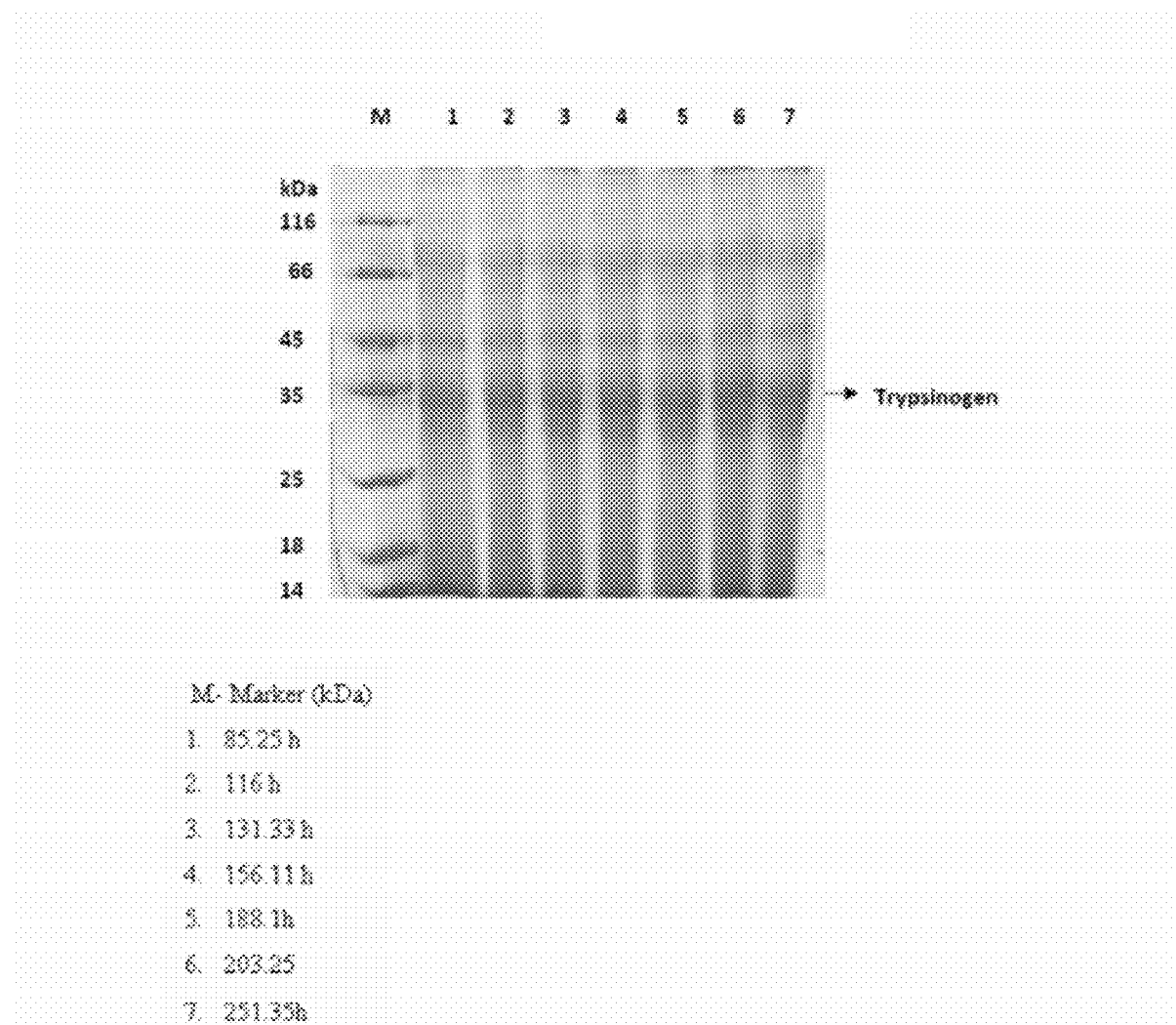

FIG. 10: Analysis of the broth supernatant on SDS PAGE. (All samples were loaded 15 µl)

Figure 11:
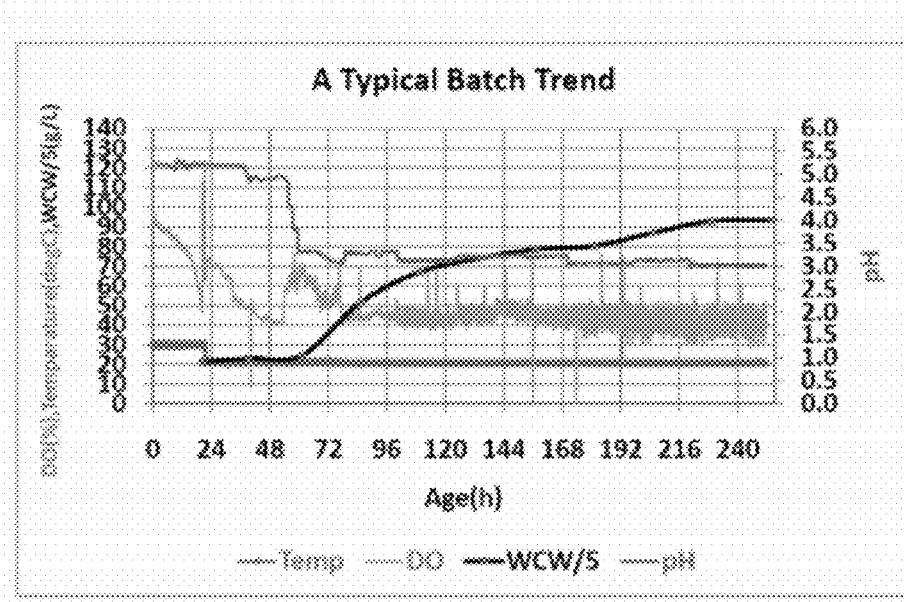

FIG. 11: Typical trends of the fermenter run: (T, pH, DO, WCW)

(T=temperature, DO=dissolved oxygen, WCW=wet cell weight)

DETAILED DESCRIPTION OF THE INVENTION

The present invention relates to a fusion polypeptide comprising at least one serine protease fused to a lipase signal sequence, said fusion polypeptide being expressed in a methyloptropic yeast wherein said fusion polypeptide has an amino acid sequence at least 80 percent homologous to SEQ ID NO: 2.

The present invention relates to a fusion polypeptide comprising at least one serine protease fused to a lipase signal sequence, said fusion polypeptide being expressed in a methyloptropic yeast wherein said fusion polypeptide has nucleotide sequence at least 80 percent homologous to SEQ ID NO: 1.

In an embodiment of the present invention, the amino acid at numbers 68 and 69 of SEQ ID NO: 2 are replaced with amino acids arginine and lysine.

In another embodiment of the present invention, the amino acid at numbers 68 is replaced with tyrosine.

In yet another embodiment of the present invention, the polypeptide enables conversion of the precursor form of insulin or insulin analogs or insulin derivatives to their corresponding active forms affording a step yield of at least 50%.

In still another embodiment of the present invention, the methylotrophic yeast belongs to *Pichia* sp.

In still another embodiment of the present invention, the methylotrophic yeast is *Pichia pastoris*.

The present invention relates to a method of expressing a fusion polypeptide comprising at least one serine protease fused to a lipase signal sequence produced from a methylotrophic yeast said fusion polypeptide having a nucleotide sequence that is at least 80% homologous to the nucleotide sequence represented by SEQ ID NO: 1 or amino acid sequence represented by SEQ ID NO: 2.

In an embodiment of the present invention, the serine protease is trypsinogen.

In another embodiment of the present invention, the methylotrophic yeast belongs to *Pichia* sp.

In yet another embodiment of the present invention, methylotrophic yeast is *Pichia pastoris*.

The present invention relates to a vector comprising sequence as described above.

The present invention relates to a transformed cell comprising sequence as described above in an expressible form.

Isolated nucleic acid molecules corresponding to novel Prolipase-Bovine trypsinogen (PLBTR) fusion protein nucleic acid sequences are provided. Additionally, amino acid sequences corresponding to the polynucleotides are encompassed. In particular, the present invention provides for isolated nucleic acid molecules comprising nucleotide sequences encoding the amino acid sequences shown in SEQ ID NO: 1. Further provided are Prolipase-Bovine trypsinogen having an amino acid sequence encoded by a nucleic acid molecule described herein—SEQ ID NO: 2.

Preferred fused trypsin serine protease-like proteins possess at least one biological activity possessed by naturally occurring trypsin serine protease-like proteins.

Variant nucleic acid molecules and polypeptides substantially homologous to the nucleotide and amino acid sequences set forth in the sequence listings are encompassed by the present invention. Additionally, fragments and substantially homologous fragments of the nucleotide and amino acid sequences are provided.

The present invention also provides vectors and host cells for recombinant expression of the nucleic acid molecules described herein, as well as methods of making such vectors and host cells and for using them for production of the polypeptides or peptides of the invention by recombinant techniques.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Reference will now be made in detail to the presently preferred embodiments of the invention which, together with the following example, serve to explain the principles of the invention.

The Examples which follow are set forth to aid in understanding the invention but are not intended to, and should not be construed to, limit its scope in any way. The Examples do not include detailed descriptions for conventional methods employed in the construction of vectors, the insertion of genes encoding polypeptides into such vectors or the introduction of the resulting plasmids into hosts. The Examples also do not include detailed description for conventional methods employed for assaying the polypeptides produced by such host vector systems. Such methods are well known to those of ordinary skill in the art and are described in numerous publications including by way of examples.

Standard techniques are used for various recombinant DNA techniques, transformation (e.g., electroporation, lipofection) and assays. The recombination techniques and procedures are generally performed according to conventional methods well known in the art and as described in various general and more specific references that are cited and discussed throughout the present specification. See e.g., Sambrook et al. Molecular Cloning: A Laboratory Manual (3rd ed., Cold Spring Harbor Laboratory Press, Cold Spring Harbor, N.Y. (2001)), which is incorporated herein by reference.

In describing and claiming the present invention, the following terminology will be used in accordance with the definitions set out herein.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of molecular and cellular biology, biochemistry, protein and nucleic acid chemistry and hybridization described herein are those well known and commonly used in the art. The methods and techniques of the present invention are generally performed according to conventional methods well known in the art.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "vector" refers to a nucleic acid molecule capable of transporting another nucleic acid to which it has been linked. The term "expression vector" includes plasmids, cosmids or phages capable of synthesizing the subject proteins encoded by their respective recombinant genes carried by the vector. Preferred vectors are those capable of autonomous replication and/or expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

The term "recombinant", as used herein to describe a protein or polypeptide means a polypeptide produced by expression of a recombinant polynucleotide. The term "recombinant", as used herein in reference to cells, means cells that can be or have been used as recipients for recombinant vectors or other transfer DNA, and include progeny of the original cell which has been transfected. It shall be understood that progeny of a single parental cell may not be completely identical in morphology or in genomic or total DNA complement to the original parent, due to accidental or deliberate mutation. Progeny of a parental cell which are sufficiently similar to the parent to be characterized by a relevant property, such as the presence of a nucleotide sequence encoding a desired polypeptide, are also considered progeny.

A "gene of interest" (GOI) is any nucleic acid sequence for which increased transcriptional expression is desired. The GOI may encode a functional nucleic acid molecule (e.g., RNA, such as an antisense RNA molecule) or, more typically, encodes a peptide, polypeptide or protein for which increased production is desired. The vectors of the invention can be used to express a "heterologous" protein. As used herein, the term "heterologous" means a nucleic acid sequence or polypeptide that originates from a foreign species, or that is substantially modified from its original form if from the same species. Furthermore, a modified or unmodified nucleic acid sequence or polypeptide that is not normally expressed in a cell is considered heterologous. Vectors of the invention can have one or more GOIs, inserted at the same or different insertion site, where each GOI is operably linked to a regulatory nucleic acid sequence which allows expression of the GOI.

Prolipase acts as an N-terminal extension of lipase, distinct from the signal sequence which is necessary for the transport of the protein into or through the membrane, or for its secretion into the extracellular medium. The 69 amino acid propeptide region of the *Rhizopus oryzae* lipase immediately follows the 26-amino acid signal sequence. Previous studies have shown that a mutation (C56 to S) in the prolipase region slows down the folding of lipase (Beer H. D., Wohlfahrt G., Schmid R. D., McCarthy J. E. G., Biochem. J. 319:351-359, 1996). The replacement of proregion of native bovine trypsinogen with prolipase region from *Rhizopus oryzae* lipase, surprisingly improved the stability and the yield of the recombinant bovine trypsinogen.

The "operational elements," as discussed herein, include at least one promoter, at least one operator, at least one leader sequence, at least one Shine-Dalgarno sequence, at least one terminator codon, and any other DNA sequences necessary or preferred for appropriate transcription and subsequent translation of the vector DNA. In particular, it is contemplated that such vectors will contain at least one origin of replication recognized by the host microorganism along with at least one selectable marker and at least one promoter sequence capable of initiating transcription of the DNA sequence. It is additionally preferred that the vector, in one embodiment, contains certain DNA sequences capable of functioning as regulators, and other DNA sequences capable of coding for regulator protein. These regulators, in one embodiment, serve to prevent expression of the DNA sequence in the presence of certain environmental conditions and, in the presence of other environmental conditions, allow transcription and subsequent expression of the protein coded for by the DNA sequence.

As used herein "amino acid" refers to peptide or protein sequences or portions thereof. The terms "protein", "peptide" and "polypeptide" are used interchangeably.

The present invention provides novel fused Prolipase-trypsin serine protease molecules. By "prolipase-trypsin serine protease molecule" is intended a novel sequence referred to as PLBTR, and variants and fragments thereof. These full-length gene sequences or fragments thereof are referred to as "PLBTR" sequences, indicating they share sequence similarity with trypsin serine protease genes. Isolated nucleic acid molecules comprising nucleotide sequences encoding the PLBTR polypeptide whose amino acid sequence is given in SEQ ID NO: 2, or a variant or fragment thereof, are provided. A nucleotide sequence encoding the PLBTR polypeptide is set forth in SEQ ID NO: 1. The sequences are members of the trypsin serine protease family.

To express the fusion proteins of the present invention, the nucleic acids can be operably linked to signals that direct gene expression. A nucleic acid is "operably linked" when it is placed into a functional relationship with another nucleic acid sequence. For instance, a promoter or enhancer is operably linked to a coding sequence if it affects the transcription of the sequence. Generally, "operably linked" means that the nucleic acid sequences being linked are contiguous and, where necessary to join two protein coding regions, contiguous and in reading frame.

It will be generally desirable to employ a promoter and/or enhancer that effectively directs the expression of a recombinant nucleic acid sequence in the host cell type chosen for expression. Those of skill in the art of molecular biology generally know the use of promoters, enhancers, and cell type combinations for recombinant polypeptide expression (for example, see Sambrook et al., 1989, infra). The control sequences employed may be constitutive, tissue-specific, inducible, and/or useful under the appropriate conditions to direct high level expression of a recombinant nucleic acid sequence, such as is advantageous in the large-scale production of recombinant polypeptides.

Preferably, the fusion polypeptide of the present invention has an amino acid sequence which is at least 65 percent similar to SEQ ID NO: 2. More preferably the similarity to SEQ ID NO: 2 of the amino acid sequence of a carrier polypeptide of the present invention is about 66 percent, more preferably 67 percent, more preferably 68 percent, more preferably 69 percent, more preferably 70 percent, more preferably 71 percent, more preferably 72 percent, more preferably 73 percent, more preferably 74 percent, more preferably 75 percent, more preferably 76 percent, more preferably 77 percent, more preferably 78 percent, more preferably 79 percent, more preferably 80 percent, more preferably 81 percent, more preferably 82 percent, more preferably 83 percent, more preferably 84 percent, more preferably 85 percent, more preferably 86 percent, more preferably 87 percent, more preferably 88 percent, more preferably 89 percent, more preferably 90 percent, more preferably 91 percent, more preferably 92 percent, more preferably 93 percent, more preferably 94 percent, more preferably 95 percent, more preferably 96 percent, more preferably 97 percent, more preferably 98 percent, more preferably 99 percent, and most preferably 100 percent.

Most preferably, the fusion polypeptide of the present invention has an amino acid sequence which is identical to SEQ ID NO: 2.

A recombinant expression system is selected from prokaryotic and eukaryotic hosts. Eukaryotic hosts include yeast cells (e.g., *Saccharomyces cerevisiae* or *Pichia pastoris*), mammalian cells or plant cells. Bacterial and eukaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells. The choice of the expression system depends on the features desired for the expressed polypeptide.

Consequently, the subject of the present invention is a expression system or cassette which is functional in a cell derived from a yeast selected from the group consisting of strain *Pichia* especially selected from the group consisting of *Pichia pastoris, Pichia methanolica* and *Schizosaccharomyces pombe* and allowing the expression of the desired polypeptide thereof encoding the protein fragments thereof, placed under the control of the elements necessary for its expression.

The host cell is preferably transformed or transfected with an expression vector which comprises the recombinant polynucleotide, and which further comprises and at least one expression control sequence which is operatively linked to the recombinant polynucleotide, and which is capable of controlling expression of the recombinant polynucleotide in the host cell so as to enable production of the soluble fusion protein thereby.

Most preferably related to aspects to the present inventions, the most preferred host cells are methylotrophic yeasts. Strains of a methylotrophic yeast which can be modified using the present invention include, but are not limited to, yeast strains capable of growing on methanol, such as yeasts of the genera *Pichia, Candida, Hansenula*, or *Torulopsis*. Preferred methylotrophic yeasts are of the genus *Pichia*. Methylotrophic yeast strains which can be modified using the present methods also include those methylotrophic yeast strains which have been engineered to express one or more heterologous proteins of interest.

As used herein, the terms "transformed" and "stably transformed" refers to a cell that has been made to incorporate a non-native (heterologous) polynucleotide sequence integrated into an episomal plasmid that is maintained for at least two generations.

As used herein, "recombinant" includes reference to a cell or vector, that has been modified by the introduction of a heterologous nucleic acid sequence or that the cell is derived from a cell so modified.

Vectors may be transformed into host cells by means including, but not limited to electroporation, viral infection, calcium phosphate precipitation, DEAE-dextran, direct microinjection, DNA-loaded liposomes and lipofectamine-DNA complexes, cell sonication, gene bombardment using high velocity microprojectiles or any other means described herein or known in the art. The vector may further comprise DNA sequences encoding functions facilitating gene expression, typically a promoter, transcription initiation sites, and transcription termination and polyadenylation functions.

The invention is also directed to a method of producing a desired protein comprising fermenting, under conditions and in a medium suitable for producing such a protein compound or its analogue, in an organism such as *Pichia* sp, in which the genes encoding polypeptides sufficient to direct the production of the desired end product has been incorporated.

According another aspect, the invention relates to a method of recombinantly producing bovine trypsin, the process comprising
(a) transforming a host with a recombinant DNA vector which comprises a DNA sequence encoding bovine trypsinogen or a derivative thereof fused to a prolipase encoding nucleotide sequence.
(b) culturing the transformed host in a suitable culture medium under conditions conducive to the expression of bovine trypsinogen and secretion thereof to the medium, and
(c) Recovering the bovine trypsinogen or trypsin or derivative thereof from the medium.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The invention will be more fully described and understood with reference to the following examples, which are given by way of illustration and are not intended to limit the scope of the invention in any way.

One of ordinary skill in the art will possess the necessary expertise to obtain and utilize a suitable expression vector for producing a soluble fusion protein of the present invention, depending on the application and purpose. Relevant general guidance relating to obtaining and utilizing expression vectors which can be used to transform or transfect host cells so as to enable these to express a recombinant polypeptide is provided herein below. Most preferably, obtaining and utilizing an expression vector of the present invention is performed according to the guidelines provided in the Examples section, below. As is described and illustrated in the Examples of the Examples section which follows, a fusion protein of the present invention can be suitably expressed by a host cell of the present invention which is transformed with an expression vector.

Thus, the present invention further provides a host cell transfected or transformed with the recombinant polynucleotide and/or expression vector. The expression vector may be obtained in any of various ways routinely practiced by the ordinarily skilled artisan, depending on the application and purpose.

The present invention is further described with the help of the following examples and figures. However, these examples should not be construed to limit the scope of the invention.

Example 1

The Nucleotide sequence of Prolipase-Bovine Trypsinogen fusion protein is represented in SEQ ID NO: 1 and the corresponding amino acid sequence is represented in SEQ ID NO: 2.

Prolipase gene fragment was amplified from *Rhizopus oryzae* lipase/pPIC9K vector using high fidelity PWO polymerase and the following primers:

```
SEQ ID NO: 4: PRORHILIPFP2 =
5'CTC GAG AAA AGA GAG GCT GAA GCT GTT CCT

GTT TCT GGT AAA TC 3'

SEQ ID NO: 5:PLBTRRP =
5' TTG TCA TCG TCA TCG GCG CTG TTG GTA GAT

CCA GA 3'
```

Bovine Trypsinogen gene was amplified from Bovine trypsinogen/TA vector using high fidelity PWO polymerase and the following primers: This Bovine trypsinogen gene was codon optimized using Entechelon web based software used for codon optimization.

```
SEQ ID NO: 6: PLBTRFP =
5' CTA CCA ACA GCG CCG ATG ACG ATG ACA AGA

TTG TCG GA 3'

SEQ ID NO: 7: BTRPRP1 =
5' GCG GCC GCT TAG TTA GAC GCA ATT GTT TGC

TTG 3'
```

Both these products were purified using Qiagen gel extraction kit. Two μls each of these purified products were used as templates. Overlapping PCR was carried to fuse Prolipase and Bovine Trypsinogen coding sequences in-frame using the following primers. The fused product was named PLBTR.

```
SEQ ID NO: 4: PRORHILIPFP2 =
5' CTC GAG AAA AGA GAG GCT GAA GCT GTT CCT

GTT TCT GGT AAA TC 3'

SEQ ID NO: 7: BTRPRP1 =
5'GCG GCC GCT TAG TTA GAC GCA ATT GTT TGC

TTG 3'
```

The resulting PCR product was analyzed on 1% agarose gel.

The correct sized gene product was excised from the above agarose gel and purified by gel extraction. The product was ligated into pTZ57R/T vector at 16° C. overnight. The ligation mix was transformed into the competent *E. coli* DH5α cells, selected the colonies on LB agar plate containing 100 μg/ml ampicillin. The colonies obtained were screened using boiling miniprep method. The presence of insert was confirmed by releasing the insert digesting with restriction enzymes XbaI and BamHI. Clone #11 was selected and more plasmid was isolated using Qiagen miniprep kit.

Example 2

Sub-Cloning the Product into pPIC9K

PLBTR fragment was excised using XhoI and EcoRI sites and ligated into pPIC9K in identical sites. The ligation mix was transformed into the competent *E. coli* DH5α cells, selected the colonies on LB agar plate containing 100 µg/ml ampicillin. The colonies obtained were screened using boiling miniprep method. The presence of insert was confirmed by releasing the insert digesting with restriction enzymes XhoI and EcoRI. The correct clone named PLBTR/pPIC9k was authenticated by restriction digestion.

*Pichia pastoris* GS115 strain transformation with PLBTR/pPIC9K plasmid:

PLBTR/pPIC9K vector was linearized using SacI and transformed into *Pichia pastoris* GS115 by electroporation by following the protocol described in Invitrogen manual. Approximately 1200 colonies were screened on 0.5 mg/ml of G418. Forty-one colonies were found to be resistant to 0.5 mg/ml of G418. These were plated on 2 mg/ml of G418.

All the six resistant colonies were checked for the presence of genomic integration of the gene of interest. These clones were studied for induction of Prolipase-Bovine trypsinogen fusion protein expression.

Following table compiles all the screening data

| No of CFU's | 0.5 mg/ml G418r CFU's | 2 mg/ml G418r CFU's | PCR confirmed |
|---|---|---|---|
| 1200 | 41 | 6 | 6 |

Screening for Mut+ and Mut$^s$:

PCR screening for Mut+ and Mut− transformants was carried out using AOX promoter FP and AOX terminator RP primers.

Small Scale Expression Studies in GS115:

A small scale expression study was carried out in shake flasks. Briefly, the clones were grown at 30° C. in BMGY followed by induction with methanol in BMMY at 30° C. Induction with methanol was carried out for a total of 3 days. Six clones were taken for expression studies. Briefly, the clones were grown at 30° C. in BMGY followed by induction with methanol in BMMY at 30° C. Induction with methanol was carried out for a total of 3 days.

Example 3

Expression of *Pichia* Codon Optimized Prolipase-Bovine Trypsinogen (CPLBTR) in In-House *Pichia* Pastoris Strains Synthetic gene for *Pichia* codon optimized Prolipase-Bovine Trypsinogen fusion protein (CPLBTR) is represented in SEQ ID: 3.

Cloning of Trypsinogen in pMBL210.

1. PCR Amplification:

PCR amplification of Prolipase-Bovine Trypsinogen was carried out using plasmid 0900098 Seq 3 pMA obtained from Geneart using primers CPLBTRFP and CPLBTRRP.

SEQ ID NO: 8: CPLBTRFP:
5' ACC TCG AGA AGA GAG TTC CAG T 3'

SEQ ID NO: 9: CPLBTRRP:
5' GGG AAT TCT TAG TTA GAA GCG ATA GTT TGC 3'

PCR Reaction Mix:

| Water | 37 µls |
|---|---|
| 0900098 Seq 3 pMA | 1.5 µls (50 ngs) |
| dNTP mix | 5 µls |
| CPLBTRFP | 1 µl (0.01 µmol) |
| CPLBTRRP | 1 µl (0.01 µmol) |
| 10 X Expand High Fidelity assay buffer | 5 µls |
| Expand high Fidelity polymerase | 0.5 µl |
| Total volume | 50 µls |

PCR Conditions:

| Initial denaturation (1 Cycle) | Amplification (30 Cycles) | Final extension (1 Cycle) |
|---|---|---|
| 94° C. for 5 minutes | 94° C. for 40 seconds<br>58° C. for 40 seconds<br>72° C. for 90 seconds | 72° C. for 10 minutes |

PCR product was analyzed on 1% agarose gel.

This PCR product has full length CPLBTR coding sequence.

Poly 'A' Tailing:

| Water | 5.5 µl |
|---|---|
| Taq buffer | 1.5 µl |
| dATP's | 1.5 µl |
| CPLBTR Fragment | 6 µl |
| Taq DNA polymerase | 0.5 µl |
| Total volume | 15 µl |

The above reaction mix was incubated at 72° C. for 20 minutes.

After 'A' tailing it is used as insert for TA ligation.

2. TA Ligation

Vector—pTZ57R/T (2894 bps) 55 ngs/µl

Insert—'A' tailing was done for PCR product CPLBTR (1050 bp) and then ligated into TA vector.

Ligation Reaction:

Ligation Reaction Mix:

| 5X ligase buffer | 4 µl |
|---|---|
| TA Vector | 4 µl |
| Insert | 11 µl |
| T 4 DNA ligase | 1 µl |
| Total volume | 20 µl |

Ligation reaction mix was incubated overnight at 16° C.

3. Transformation:

Ligation mix was used to transform into chemical competent *E. coli* DH5 alpha cells using heat shock method. Regeneration mix was plated on to the LB agar plates containing 100 µgs/ml of ampicillin. Plates were incubated at 37° C. overnight.

4. Screening:

Twenty four clones were screened by colony PCR using flanking vector primers M13FP and M13RP. Expected amplicon size was 1180 bps. Eighteen clones were found to be positive. Plasmid DNA was prepared from Clone#2 for further analysis.

Example 4

Subcloning of CPLBTR into pMBL210

1. Ligation:
Vector—pMBL210 (5422 bps) digested with XhoI and EcoRI restriction enzymes, gel purified the vector band 40 ngs/µl.
Insert—CPLBTR/TA was digested with XhoI and EcoRI—55 ngs/µl.
Ligation Reaction Mix:

| | |
|---|---|
| Water | 4 µl |
| 10 X ligase buffer | 2 µl |
| Vector | 5 µl |
| Insert | 8 µl |
| T 4 DNA ligase | 1 µl |
| Total volume | 20 µl |

Ligation reaction set up was incubated overnight at 16° C. pMBL 210 Vector details have been represented in.

| | |
|---|---|
| F1(IG) | 2-457 bps |
| AOX1 Promoter | 615-1575 bps |
| Mat α Signal sequence | 1593-1865 bps |
| PIC forward primer binding region | 1801-1820 bps |
| PIC forward primer sequence | 5'CTA TTG CCA GCA TTG CTG CT 3' |
| PIC reverse primer binding region | 1913-1932 bps |
| PIC reverse primer sequence | 5'TGC CCA ACT TGA ACT GAG GA 3' |
| AOX Terminator | 1890-2230 bps |
| pTEF1 promoter | 2262-2673 bps |
| PEM7 | 2674-2741 bps |
| Zeocin marker | 2742-3116 bps |
| Ampicillin marker | 4419-5279 bps |

The vector used for the production of PLBTR in *P. pastoris* is pMBL 210 (5422 bps), which is a derivative of pTZ57R vector. Some of the features of this vector are:

AOX1 Promoter: A ~960 bp fragment containing the AOX1 promoter isolated from BICC #9450 which allows methanol inducible high level expression in *Pichia pastoris* and also targets plasmid integration to the AOX1 locus.

α-Factor signal sequence: a 270 bp fragment encoding the *S. cerevisiae* Mat α-factor signal sequence, which allows secretion of desired protein into the medium.

MCS: Multiple cloning sites which allows cloning of the desired gene into the expression vector. The unique restriction sites for cloning in frame with the α-factor secretion signal are XhoI, EcoRI.

Two restriction sites: Bgl II and Sac I for the linearization of vector which assists in efficient integration into the *Pichia* genome 3' AOX1 terminator: A 340 bps sequence from the AOX1 gene which is further 3' to the TT sequence and targets plasmid integration at the AOX1 locus.

Zeocin marker: Allows selection of transformants in *Pichia pastoris*

Ampicillin resistance gene: allows selection and maintenance of vector in *E. coli*.

2. Transformation:
Ligation mix was used to transform into chemical competent *E. coli* DH5 alpha cells using heat shock method. Regeneration mix was plated on to LB agar plates containing 25 ugs/ml of Zeocin. Plates were incubated at 37° C. overnight.

3. Screening:
Twenty clones were screened by colony PCR using flanking vector primers, PICFP and PICRP. Expected amplicon size was 1128 bps. Eighteen clones were positive. Plasmid DNA was prepared from clone #3 for further analysis.

4. Analysis of Recombinant Plasmid:
CPLBTR/pMBL 210 clone #3 was analyzed by restriction digestion and submitted for sequencing.

Example 5

[B] Expression of Prolipase Bovine Trypsinogen in *Pichia Pastoris*

1. Transformation of *P. pastoris*:
[CPLBTR/pMBL210] clone #3 plasmid DNA was digested with SacI and used to transform electrocompetent cells of *P. pastoris* in-house strains, BICC#9450, #9452 and #9453. Electroporated competent cells at 2000 volts, 200Ω and 25µF using Bio-Rad Gene Pulsor XL. Regeneration mix was plated onto YNBD plates and incubated at 30° C. for 48 hours.

Example 6

Screening for Multicopy Integrants

Approximately 1000 transformants from BICC #9450, 200 transformants from BICC #9452 and 600 transformants from BICC #9453 were inoculated in YPD broth in 96 well microtitre plates along with appropriate controls. The plates were incubated at 30° C. for 24 hours and then stamped onto YPD agar plates containing 2.5 mg/ml Zeocin. The plates were incubated at 30° C. for 48 hours. Ten Zeo2500 resistant colonies for BICC #9450, 4 Zeo2500 resistant colonies for #9452 and 21 Zeo2500 resistant colonies for #9453 were obtained.

Example 7

Confirmation of Gene Integration in the Genome by PCR

Genomic DNA was made from the selected recombinant *Pichia* clones by cell lysis method. PCR was carried out using vector specific primers (PICFP and PICRP) to confirm the integration of CPLBTR in the genome. BICC #9450, #9452 and #9453 host strains were used as respective negative controls.

Example 8

Small Scale Expression Studies in *P. pastoris*

Figure 9:
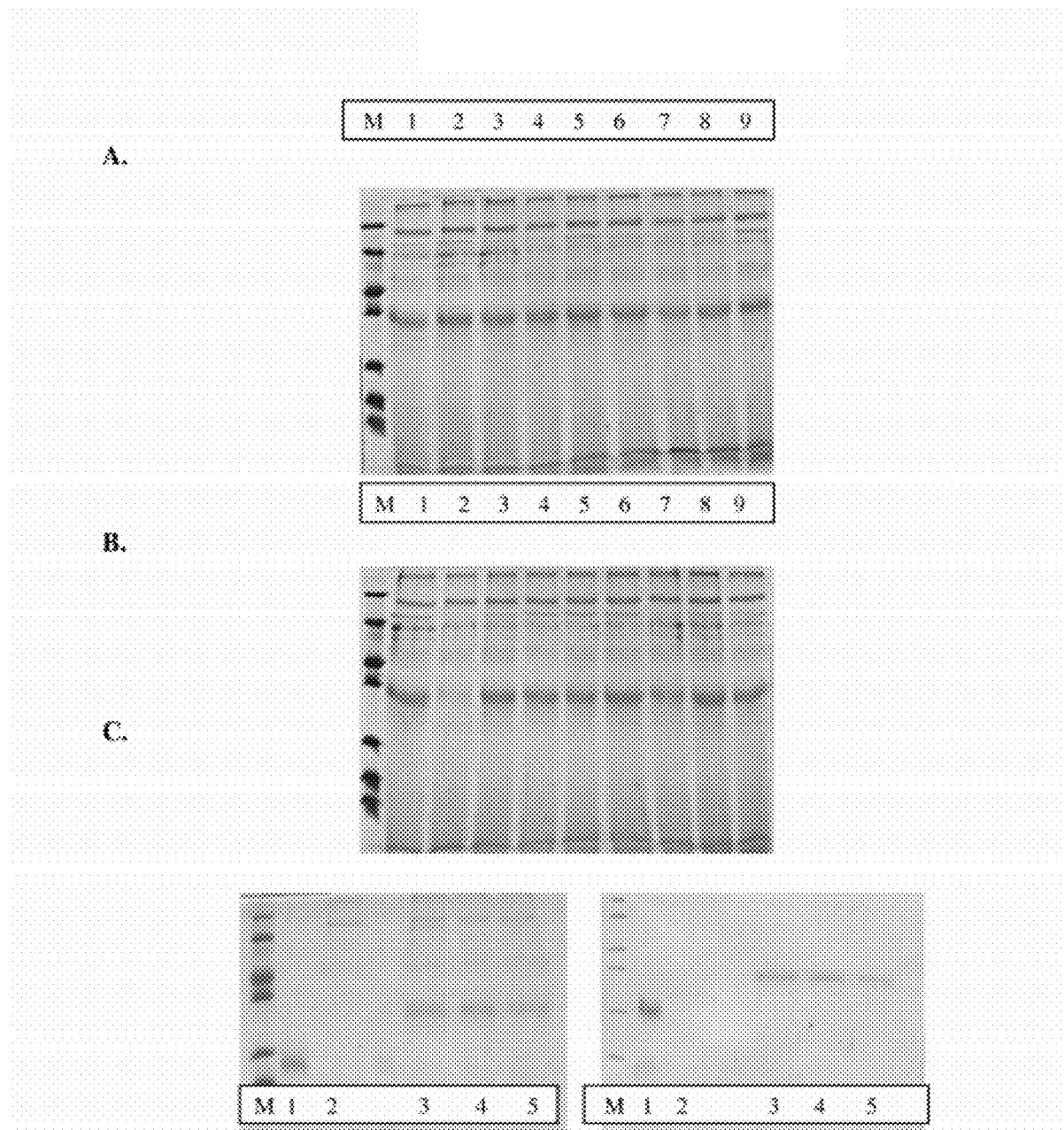

A small scale expression study was carried out in shake flasks. Briefly, the clones were grown at 30° C. in BMGY followed by induction with methanol in BMMY at 30° C. Induction with methanol was carried out for a total of 3 days. Eight clones each from BICC#9450 and #9453 and 3 clones from #9452 host were taken for expression studies. Briefly, the clones were grown at 30° C. in BMGY followed by induction with methanol in BMMY at 30° C. Induction with methanol was carried out for a total of 3 days (FIG. 9).

Example 9

Analysis of Expression

Crude supernatant from each of the clones (Day 2 and Day 3 of induction) were analyzed on SDS-PAGE stained with Coomassie blue. CPLBTR was secreted as a ~35 kDa protein.
Results:
1. It was confirmed from the above induction study that the among the three *Pichia pastoris* strains used for the expression of CPLBTR, BICC #9450 was the best.
2. CPLBTR 9450 clone #1 is giving higher titer among the eight clones of this strain tested.
3. It was decided to use this strain for all the future work.

Cell Bank Preparation:
CPLBTR 9450 Clone #1 was found to be the best in terms of productivity and Methanol consumption. This clone was given to the cell culture group to prepare Research cell bank.
RCB number assigned to CPLBTR 9450 Clone #1 is BICC #9580.

Example 10

Upstream and Downstream Process Optimization

Process Optimization:
Two clones expressing trypsinogen were evaluated for fermentation and recovery of product at 50 L scale. The detail of a generalized process is as follows:

Fermentation Medium Composition:

| Components | Quantity (g/L) |
| --- | --- |
| $CaSO_4 \cdot 2H_2O$ | 0.93 |
| $MgSO_4 \cdot 7H_2O$ | 29.8 |
| $K_2SO_4$ | 36.4 |
| KOH | 4.13 |
| Glycerol | 40 |
| $H_3PO_4$ (Density-1.7) | 22.95 |
| Urea | 6.0 |

The individual components were dissolved in minimal volume of water in the above-mentioned sequence and sterilized at 121° C. for 1 hour. The trace salt solution and D-biotin (pre-sterilized by filtration) were added aseptically to the medium, each at the rate of 4.35 ml/L of medium (density of trace salts solution is 1.05 and that of D-biotin is 1.0).

Composition of Trace Salt Solution:

| Components (Salts) | Quantity (g/L) |
| --- | --- |
| Copper sulphate, $CuSO_4 \cdot 5H_2O$ | 6.0 |
| Sodium iodide, NaI | 0.08 |
| Manganese sulphate, $MnSO_4 \cdot H_2O$ | 3.0 |
| Sodium molybdate, $Na_2MoO_4 \cdot 2H_2O$ | 0.20 |
| Boric acid, $H_3BO_3$ | 0.02 |
| Cobalt chloride, $CoCl_2 \cdot 6H_2O$ | 0.50 |
| Zinc chloride, $ZnCl_2$ | 20.0 |
| Ferrous sulphate, $FeSO_4 \cdot 7H_2O$ | 65.0 |
| Sulphuric acid, $H_2SO_4$ | 5.0 mL |

All the salts were dissolved one by one in potable water and were sterilized by filtration through sterilizing grade filtration apparatus.

Biotin Solution Preparation:
D-Biotin 0.2 g/L
Biotin was dissolved in potable water and sterilized by filtration through sterilizing grade filtration apparatus.

Yeast Extract and Soy Peptone Feed:
Additionally, Yeast Extract and Soy Peptone (YEP) feed was also added during fermentation. It is to be prepared as follows:

| Components | Conc. (g/L) |
| --- | --- |
| Soy Peptone | 200 |
| Yeast extract | 100 |

The components were dissolved and volume was made up with potable water as required. The solution was then sterilized at 121°-123° C. for 90 min. The density of YEP feed was around 1.05. The yeast extract can be replaced with derivatives of inactive/active yeast. Further, soya peptone can also be replaced with derivatives of soya bean flour/meal.

Methanol Feed:
12.0 ml of trace salt solution, 12 mL of D-biotin solutions and 40 g of Urea were added per liter of methanol before feeding.

Fermentation Process:
The fermentation process includes a batch cell growth phase, an optional glycerol fed batch phase and methanol induction phase.

Batch Cell Growth Phase
Batch Monitoring and Control
Production fermenter parameters are initially set and controlled as follows:
Temperature: 30°±2° C.
pH: 5±0.2
DO: >10%
Run Time: 22-26 hr Methanol Induction Phase (MIP)
Methanol feeding was started immediately after the end of Batch phase. Methanol was sterilized (online) by filtration using a commercially available sterilizing grade filter.
At the beginning of MIP, the pH was adjusted to 6.0±0.2 and the temperature was adjusted to about 23±2° C.
Simultaneously, another feed, yeast extract and Soy peptone feed (YEP) were also started in the fermenter at the rate of 0.4 g/L/h of starting volume.

MIP Monitoring and Control
Temperature: 23.0±2° C.
pH: 6.0±0.2
DO: >1% (used to control methanol concentration in broth)
Run Time: 10-12 days According to another aspect of the invention, the inoculum was prepared by cultivating lyophilized glycerol stock culture to minimal glycerol (MGY) medium. The basal fermentor media has been derived from "Control *Pichia* process guidelines" Invitrogen contains ortho-phosphoric acid, calcium sulfate dehydrated, potassium sulfate, magnesium sulfate hepta-hydrated, potassium hydroxide, glycerol, trace salts and D-biotin. The nutrient culture medium must also contain known compounds in small or trace amounts which are usually incorporated in fermentation culture media such as water soluble compounds of Ca, Mg, Mn, Fe, K, Co, Cu, Zn, B, Mo, Br and I. Other trace salts may also be present.

Downstream Process:

Following is the protocol for downstream:

Centrifugation:

End of fermentation broth (EOF) and partial withdrawals have to be centrifuged at 4-8° C. for 30 min at 5000 rpm.

Micro Filtration:

Carried out Microfiltration with PO 1.4 mm ID of centrifuged supernatant (CFS). pH was maintained at 3.0±0.05 (pH is very IMPORTANT) throughout the process. Concentrate it to minimum volume and carried out diafiltration with sterile water, pH 3.0. Do a diafiltration to get product from retentate.

Ultra Filtration:

Ultra filtration was done with PAN 6000 MWCO. The supernatant was concentrated to around 20 times of MF feed quantity. Diafiltration was done with sterile water (pH—3.0+/−0.05) to obtain the conductivity of final retentate close to 2+1 mS/cm at pH 3.0+0.05. Volume, conductivity & pH of Cell free supernatant and ultrafiltrate concentrate (UFC) was noted down before and after ultrafiltration.

Reagents:

A. 67 mM Sodium Phosphate Buffer, pH 7.6 at 25° C.
B. 0.25 mM Na-Benzoyl-L-Arginine Ethyl Ester Solution (BAEE)
(Prepare 50 ml in Reagent A)
C. 5 mM Hydrochloric Acid Solution (HCl)
D. 1 M Calcium Chloride Solution ($CaCl_2$)
E. 1 mM Hydrochloric Acid Solution (HCl)
F. 400 mM Tris HCl Buffer, pH 8.4 at 25° C. (Buffer)
G. 0.02% (w/v) Trypsin Enzyme Solution (Trypsin) (Immediately before use, prepare 3 ml in Reagent C using Standard Trypsin)
H. Trypsinogen Enzyme Solution (Trypsinogen) (Immediately before use, prepare a solution containing 5 mg/ml of Trypsinogen in Reagent C.)

Procedure:

Prepare an Activating Mixture by pipetting (in milliliters) the following reagents into a suitable container:

Reagent D (CaCl2)—2.00
Reagent F (Buffer)—38.00
Reagent G (Trypsin)—2.00
Mix by swirling.

Step 1: Total Trypsin Activity

At zero time add 0.1 ml of Reagent H (Trypsinogen) to 1 ml of the Activating Mixture and incubate at 5° C. for 96-120 hours. Then dilute 0.2 ml to 10.2 ml with Reagent E (HCl). Proceed with the trypsin assay.

Calculations:

The calculation shown below can be used to determine the Total Trypsin activity of the Trypsinogen.

Trypsin Activity (U/ml)=($\Delta A$253 nm/3 minute Test−$\Delta A$253 nm/3 minute Blank)×DF/(0.2*0.003*3)
DF—Dilution Factor Example 11

A 50 L fermentation batch with 12 L of initial medium volume was taken with the above mentioned protocol. Final harvested broth quantity was 25 L. Broth samples were withdrawn at different time intervals and spun at 10000 rpm to obtain clear supernatant. The supernatant was assayed by SDS-PAGE gel from third day onwards and the results are given below.

In this batch, the expression level was low as is evident from band thickness. The lower levels of key nutrients like carbon source methanol, residual phosphate as well as nitrogen source-ammonium ions (table below) could have lead to an adverse condition mounting to starving and/or leading to degradation of proteins.

| Age (h) | $PO_4$ (ppm) | $NH_4$ (ppm) | Residual Methanol conc. (g/L) |
|---|---|---|---|
| 52 | 3200 | 3400 | 0.25 |
| 64 | 2286 | 3030 | 0.15 |
| 76 | 1832 | 3462 | 0.00 |
| 88 | 1610 | 3110 | 0.10 |
| 100 | 1519 | 2631 | 0.05 |
| 120 | 850 | 2080 | 0.07 |
| 138 | 211 | 1961 | 0.00 |

Example 12

Another 50 L fermentation batch was taken with an aim to avoid any limitation of residual phosphate and ammonium ions. This was achieved by feeding one of the existing nutrient ortho-phosphoric acid during the methanol induction phase. The pH was allowed to drop (due to feeding of ortho-phosphoric acid) post initiation of induction. It was found that pH drops to 3.0 in a time of about 38-40 h. By following above strategy, it was possible to increase the concentration of key nitrogen source-ammonium ions as well as residual phosphates much more than that observed in previous batch (see table below). Final harvested broth quantity (End of fermentation and partial overflow) was 41 L. The broth supernatant was assayed by SDS-PAGE gel from 4th day onwards and the results are represented in FIG. 10.

Phosphate and Ammonium Trend:

| Age (h) | $PO_4$ (ppm) | $NH_4$ (ppm) | Residual Methanol conc. (g/L) |
|---|---|---|---|
| 39 | 14109 | 3246 | 0.24 |
| 60 | 10106 | 1954 | 0.16 |
| 85 | 7267 | 1164 | 0.01 |
| 91 | 16195 | 4254 | 0.00 |
| 116 | 25120 | 6100 | 0.03 |
| 131 | 30038 | 6800 | 0.04 |
| 156 | 28352 | 6500 | 0.00 |
| 188 | 30250 | 10557 | 0.01 |
| 203 | 29335 | 6262 | 0.04 |
| 227 | 23510 | 6100 | 0.00 |
| 251 | 24712 | 5993 | 0.01 |

Example 13

Applications in Insulin Downstream Process

Recombinant Trypsin Expressed in In-House *Pichia* Host: Application in Processing of Precursor of Insulin and Insulin Analogues to Product Trypsinogen was expressed in in-house *Pichia pastoris* and the fermentation was performed. The isolated Trypsinogen was activated to active Trypsin and used for the processing of Insulin and Insulin analogues like Insulin Glargine, Insulin Lispro and Insulin Aspart. In each experimental set Trypsin (r-DNA origin) from the regular vendor was used as a control sample.

The corresponding precursor form of Insulin or its analogues were taken in appropriate buffer. The reaction condition was maintained appropriately for each set of reaction condition. r-DNA origin trypsin (both in-house and sourced from vendor) was added to the corresponding reaction mixture. The reaction profile was monitored at different time interval and stopped when the step yield of the final product was maximum.

The results of the step yield of the conversion of corresponding Insulin or its analogues from its precursor form to the product form using the in-house r-DNA origin Trypsin and r-DNA Trypsin from the regular vendor was shown in the table below.

| Product | Trypsin Source | Step Yield (%) |
| --- | --- | --- |
| Insulin | In-house r-DNA Trypsin | 63 |
|  | r-DNA Trypsin from vendor | 62 |
| Insulin Glargine | In-house r-DNA Trypsin | 58 |
|  | r-DNA Trypsin from vendor | 58 |
| Insulin Lispro | In-house r-DNA Trypsin | 70 |
|  | r-DNA Trypsin from vendor | 69.3 |
| Insulin Aspart | In-house r-DNA Trypsin | 82 |
|  | r-DNA Trypsin from vendor | 79.4 |
| IN-105 | In-house r-DNA Trypsin | 77 |
|  | r-DNA Trypsin from vendor | 79 |

We claim:

1. The fusion protein consisting of the amino acid sequence set forth as SEQ ID NO: 2.

2. The nucleotide sequence set forth as SEQ ID NO: 1 or SEQ ID NO: 3.

3. A method of obtaining a fusion polypeptide comprising at least one active serine protease fused to a prolipase region wherein said fusion polypeptide consists of the amino acid sequence set forth as SEQ ID No 2, said method comprising acts of:
   a. fusing a sequence encoding a serine protease to a sequence encoding a prolipase region to obtain a fusion product (PLBTR) consisting of the nucleotide sequence set forth as SEQ ID NO: 1 or SEQ ID NO: 3
   b. inserting the fusion product into a vector and transforming a host with said vector; and
   c. culturing the host for expressing the nucleotide sequence to obtain the fusion polypeptide of ~35 kDa protein.

4. The method of claim 3, wherein the host is a methylotrophic yeast.

5. The method of claim 4, wherein said methylotrophic yeast is *Pichia pastoris*.

6. A vector comprising the nucleotide sequence set forth as SEQ ID NO: 1 or SEQ ID NO: 3.

7. A transformed host cell comprising the vector as claimed in claim 6, in an expressible form.

8. The method of claim 3, wherein said polypeptide converts a precursor form of insulin or insulin analogs or insulin derivatives to their corresponding active forms affording yields of at least 70%.

9. The transformed host cell of claim 7, wherein the host cell is a methylotrophic yeast cell.

* * * * *

SEQUENCE LISTING

<160> NUMBER OF SEQ ID NOS: 9

<210> SEQ ID NO 1
<211> LENGTH: 978
<212> TYPE: DNA
<213> ORGANISM: Artificial Sequence
<220> FEATURE:
<223> OTHER INFORMATION: Fusion from Rhizopus oryzae prolipase and
      bovine trypsinogen
<220> FEATURE:
<221> NAME/KEY: exon
<222> LOCATION: (1)..(978)

<400> SEQUENCE: 1

```
gtt cct gtt tct ggt aaa tct gga tct tcc aac acc gcc gtc tct gca        48
Val Pro Val Ser Gly Lys Ser Gly Ser Ser Asn Thr Ala Val Ser Ala
1               5                   10                  15 tct gac aat gct gcc ctc cct cct ctc atc tcc agc cgt tgt gct cct        96
Ser Asp Asn Ala Ala Leu Pro Pro Leu Ile Ser Ser Arg Cys Ala Pro
                20                  25                  30 cct tct aac aag gga agt aaa agc gat ctc caa gct gaa cct tac aac       144
Pro Ser Asn Lys Gly Ser Lys Ser Asp Leu Gln Ala Glu Pro Tyr Asn
            35                  40                  45 atg caa aag aat aca gaa tgg tat gag tcc cat ggt ggc aac ctg aca       192
Met Gln Lys Asn Thr Glu Trp Tyr Glu Ser His Gly Gly Asn Leu Thr
        50                  55                  60 tcc atc gga aag cgt gat gac aac ttg gtt ggt ggc atg act ttg gac       240
Ser Ile Gly Lys Arg Asp Asp Asn Leu Val Gly Gly Met Thr Leu Asp
65                  70                  75                  80 tta ccc agc gat gct cct cct atc agc ctc tct agc tct acc aac agc       288
Leu Pro Ser Asp Ala Pro Pro Ile Ser Leu Ser Ser Ser Thr Asn Ser
                85                  90                  95 gcc gat gac gat gac aag att gtc gga ggc tac acc tgt ggt gca aac       336
Ala Asp Asp Asp Asp Lys Ile Val Gly Gly Tyr Thr Cys Gly Ala Asn
                100                 105                 110 act gtg ccc tac caa gtg agc ctg aat tca gga tac cac ttt tgc ggt       384
Thr Val Pro Tyr Gln Val Ser Leu Asn Ser Gly Tyr His Phe Cys Gly
            115                 120                 125 ggg tca tta atc aac tcg caa tgg gtt gta tct gcc gca cat tgt tac       432
Gly Ser Leu Ile Asn Ser Gln Trp Val Val Ser Ala Ala His Cys Tyr
        130                 135                 140 aaa tca ggc att caa gtg aga ctt gga gaa gat aat att aat gtc gta       480
Lys Ser Gly Ile Gln Val Arg Leu Gly Glu Asp Asn Ile Asn Val Val
145                 150                 155                 160 gag ggt aat gaa cag ttc att agt gcc tct aaa tcc att gtt cat cct       528
Glu Gly Asn Glu Gln Phe Ile Ser Ala Ser Lys Ser Ile Val His Pro
                165                 170                 175 tct tat aat tcc aac acc ctt aac aat gat ata atg ttg ata aag cta       576
Ser Tyr Asn Ser Asn Thr Leu Asn Asn Asp Ile Met Leu Ile Lys Leu
```

```
                180                 185                 190
aag tcc gct gcc agt ttg aat tct aga gtc gct tct atc tct ctg cca     624
Lys Ser Ala Ala Ser Leu Asn Ser Arg Val Ala Ser Ile Ser Leu Pro
        195                 200                 205 act tcc tgt gca agc gct ggc act caa tgt ttg ata agt ggt tgg gga     672
Thr Ser Cys Ala Ser Ala Gly Thr Gln Cys Leu Ile Ser Gly Trp Gly
210                 215                 220 aac acg aag agt tcc ggt act agc tac cct gac gtt cta aag tgt ctc     720
Asn Thr Lys Ser Ser Gly Thr Ser Tyr Pro Asp Val Leu Lys Cys Leu
225                 230                 235                 240 aaa gct cca atc ttg tca gat tcc tca tgc aaa agt gct tat cct ggt     768
Lys Ala Pro Ile Leu Ser Asp Ser Ser Cys Lys Ser Ala Tyr Pro Gly
            245                 250                 255 cag atc aca tcg aac atg ttt tgt gct ggt tac ttg gag gga ggg aag     816
Gln Ile Thr Ser Asn Met Phe Cys Ala Gly Tyr Leu Glu Gly Gly Lys
        260                 265                 270 gat tct tgt cag gga gac tct gga ggt cca gtt gtc tgt tct gga aaa     864
Asp Ser Cys Gln Gly Asp Ser Gly Gly Pro Val Val Cys Ser Gly Lys
        275                 280                 285 tta cag ggt att gta tcg tgg ggt tca ggg tgc gca caa aag aac aaa     912
Leu Gln Gly Ile Val Ser Trp Gly Ser Gly Cys Ala Gln Lys Asn Lys
290                 295                 300 cca ggt gtt tat acc aag gtt tgc aat tat gtt tca tgg atc aag caa     960
Pro Gly Val Tyr Thr Lys Val Cys Asn Tyr Val Ser Trp Ile Lys Gln
305                 310                 315                 320 aca att gcg tct aac taa                                             978
Thr Ile Ala Ser Asn
            325

<210> SEQ ID NO 2
<211> LENGTH: 325
<212> TYPE: PRT
<213> ORGANISM: Artificial Sequence
<220> FEATURE:
<223> OTHER INFORMATION: Fusion from Rhizopus oryzae prolipase and
      bovine trypsinogen
<220> FEATURE:
<221> NAME/KEY: PEPTIDE
<222> LOCATION: (1)..(325)

<400> SEQUENCE: 2

Val Pro Val Ser Gly Lys Ser Gly Ser Ser Asn Thr Ala Val Ser Ala
1               5                   10                  15

Ser Asp Asn Ala Ala Leu Pro Pro Leu Ile Ser Ser Arg Cys Ala Pro
            20                  25                  30

Pro Ser Asn Lys Gly Ser Lys Ser Asp Leu Gln Ala Glu Pro Tyr Asn
        35                  40                  45

Met Gln Lys Asn Thr Glu Trp Tyr Glu Ser His Gly Gly Asn Leu Thr
50                  55                  60

Ser Ile Gly Lys Arg Asp Asp Asn Leu Val Gly Gly Met Thr Leu Asp
65                  70                  75                  80

Leu Pro Ser Asp Ala Pro Pro Ile Ser Leu Ser Ser Thr Asn Ser
                85                  90                  95

Ala Asp Asp Asp Lys Ile Val Gly Gly Tyr Thr Cys Gly Ala Asn
                100                 105                 110

Thr Val Pro Tyr Gln Val Ser Leu Asn Ser Gly Tyr His Phe Cys Gly
            115                 120                 125

Gly Ser Leu Ile Asn Ser Gln Trp Val Val Ser Ala Ala His Cys Tyr
        130                 135                 140
```

```
Lys Ser Gly Ile Gln Val Arg Leu Gly Glu Asp Asn Ile Asn Val Val
145                 150                 155                 160

Glu Gly Asn Glu Gln Phe Ile Ser Ala Ser Lys Ser Ile Val His Pro
                165                 170                 175

Ser Tyr Asn Ser Asn Thr Leu Asn Asn Asp Ile Met Leu Ile Lys Leu
            180                 185                 190

Lys Ser Ala Ala Ser Leu Asn Ser Arg Val Ala Ser Ile Ser Leu Pro
        195                 200                 205

Thr Ser Cys Ala Ser Ala Gly Thr Gln Cys Leu Ile Ser Gly Trp Gly
    210                 215                 220

Asn Thr Lys Ser Ser Gly Thr Ser Tyr Pro Asp Val Leu Lys Cys Leu
225                 230                 235                 240

Lys Ala Pro Ile Leu Ser Asp Ser Ser Cys Lys Ser Ala Tyr Pro Gly
                245                 250                 255

Gln Ile Thr Ser Asn Met Phe Cys Ala Gly Tyr Leu Glu Gly Gly Lys
            260                 265                 270

Asp Ser Cys Gln Gly Asp Ser Gly Gly Pro Val Val Cys Ser Gly Lys
        275                 280                 285

Leu Gln Gly Ile Val Ser Trp Gly Ser Gly Cys Ala Gln Lys Asn Lys
    290                 295                 300

Pro Gly Val Tyr Thr Lys Val Cys Asn Tyr Val Ser Trp Ile Lys Gln
305                 310                 315                 320

Thr Ile Ala Ser Asn
                325

<210> SEQ ID NO 3
<211> LENGTH: 975
<212> TYPE: DNA
<213> ORGANISM: Artificial Sequence
<220> FEATURE:
<223> OTHER INFORMATION: Synthetically generated codons for a fusion of
      Rhizopus oryzae prolipase and bovine trypsinogen
<220> FEATURE:
<221> NAME/KEY: exon
<222> LOCATION: (1)..(975)

<400> SEQUENCE: 3 gtt cca gtt tct ggt aag tct ggt tcc tcc aac act gct gtt tct gct      48
Val Pro Val Ser Gly Lys Ser Gly Ser Ser Asn Thr Ala Val Ser Ala
1               5                   10                  15 tcc gat aac gct gct ttg cca cca ttg atc tct tct aga tgt gct cca      96
Ser Asp Asn Ala Ala Leu Pro Pro Leu Ile Ser Ser Arg Cys Ala Pro
            20                  25                  30 cca tct aac aag ggt tcc aag tcc gat ttg cag gct gaa cca tac aac     144
Pro Ser Asn Lys Gly Ser Lys Ser Asp Leu Gln Ala Glu Pro Tyr Asn
        35                  40                  45 atg cag aaa aac act gag tgg tac gaa tct cac ggt ggt aac ttg act     192
Met Gln Lys Asn Thr Glu Trp Tyr Glu Ser His Gly Gly Asn Leu Thr
    50                  55                  60 tcc atc gga aag aga gat gac aac ttg gtt ggt gga atg act ttg gac     240
Ser Ile Gly Lys Arg Asp Asp Asn Leu Val Gly Gly Met Thr Leu Asp
65                  70                  75                  80 ttg cca tct gac gct cca cca att tct ttg tcc tct tcc act aac tct     288
Leu Pro Ser Asp Ala Pro Pro Ile Ser Leu Ser Ser Ser Thr Asn Ser
                85                  90                  95 gct gat gac gac gac aag atc gtt ggt ggt tac act tgt ggt gct aac     336
Ala Asp Asp Asp Asp Lys Ile Val Gly Gly Tyr Thr Cys Gly Ala Asn
            100                 105                 110 act gtt cca tac cag gtt tca ttg aac tcc gga tac cac ttt tgt ggt     384
```

```
                Thr Val Pro Tyr Gln Val Ser Leu Asn Ser Gly Tyr His Phe Cys Gly
                        115                 120                 125 ggt tcc ttg att aac tcc cag tgg gtt gtc tct gct gct cac tgt tac         432
Gly Ser Leu Ile Asn Ser Gln Trp Val Val Ser Ala Ala His Cys Tyr
            130                 135                 140 aag tcc ggt atc caa gtt aga ttg gga gag gac aac atc aac gtt gtt         480
Lys Ser Gly Ile Gln Val Arg Leu Gly Glu Asp Asn Ile Asn Val Val
145                 150                 155                 160 gag ggt aac gag caa ttc att tcc gct tcc aag tcc att gtt cac cca         528
Glu Gly Asn Glu Gln Phe Ile Ser Ala Ser Lys Ser Ile Val His Pro
                165                 170                 175 tcc tac aac tcc aac act ttg aac aac gac atc atg ttg atc aag ttg         576
Ser Tyr Asn Ser Asn Thr Leu Asn Asn Asp Ile Met Leu Ile Lys Leu
            180                 185                 190 aag tcc gct gct tct ttg aac tct aga gtt gct tcc atc tcc ttg cca         624
Lys Ser Ala Ala Ser Leu Asn Ser Arg Val Ala Ser Ile Ser Leu Pro
195                 200                 205 act tca tgt gct tcc gct ggt act caa tgt ttg atc tcc gga tgg ggt         672
Thr Ser Cys Ala Ser Ala Gly Thr Gln Cys Leu Ile Ser Gly Trp Gly
                210                 215                 220 aac act aag tcc tct ggt act tcc tac cca gac gtt ttg aag tgt ttg         720
Asn Thr Lys Ser Ser Gly Thr Ser Tyr Pro Asp Val Leu Lys Cys Leu
225                 230                 235                 240 aag gct cca att ttg tct gac tcc tcc tgt aag tct gct tac cca gga         768
Lys Ala Pro Ile Leu Ser Asp Ser Ser Cys Lys Ser Ala Tyr Pro Gly
                245                 250                 255 caa atc act tcc aac atg ttc tgt gct ggt tac ttg gaa ggt gga aag         816
Gln Ile Thr Ser Asn Met Phe Cys Ala Gly Tyr Leu Glu Gly Gly Lys
            260                 265                 270 gac tct tgt cag gga gat tct ggt ggt cca gtt gtt tgt tcc ggt aag         864
Asp Ser Cys Gln Gly Asp Ser Gly Gly Pro Val Val Cys Ser Gly Lys
275                 280                 285 ttg cag ggt att gtt tct tgg ggt tcc ggt tgt gct caa aag aac aag         912
Leu Gln Gly Ile Val Ser Trp Gly Ser Gly Cys Ala Gln Lys Asn Lys
                290                 295                 300 cct ggt gtt tac act aaa gtt tgt aac tac gtt tcc tgg atc aag caa         960
Pro Gly Val Tyr Thr Lys Val Cys Asn Tyr Val Ser Trp Ile Lys Gln
305                 310                 315                 320 act atc gct tct aac                                                     975
Thr Ile Ala Ser Asn
                325

<210> SEQ ID NO 4
<211> LENGTH: 44
<212> TYPE: DNA
<213> ORGANISM: Artificial Sequence
<220> FEATURE:
<223> OTHER INFORMATION: A synthetic primer

<400> SEQUENCE: 4
ctcgagaaaa gagaggctga agctgttcct gtttctggta aatc                        44

<210> SEQ ID NO 5
<211> LENGTH: 35
<212> TYPE: DNA
<213> ORGANISM: Artificial Sequence
<220> FEATURE:
<223> OTHER INFORMATION: A synthetic primer

<400> SEQUENCE: 5
ttgtcatcgt catcggcgct gttggtagat ccaga                                  35
```

```
<210> SEQ ID NO 6
<211> LENGTH: 38
<212> TYPE: DNA
<213> ORGANISM: Artificial Sequence
<220> FEATURE:
<223> OTHER INFORMATION: A synthetic primer

<400> SEQUENCE: 6
ctaccaacag cgccgatgac gatgacaaga ttgtcgga                            38

<210> SEQ ID NO 7
<211> LENGTH: 33
<212> TYPE: DNA
<213> ORGANISM: Artificial Sequence
<220> FEATURE:
<223> OTHER INFORMATION: A synthetic primer

<400> SEQUENCE: 7
gcggccgctt agttagacgc aattgtttgc ttg                                 33

<210> SEQ ID NO 8
<211> LENGTH: 22
<212> TYPE: DNA
<213> ORGANISM: Artificial Sequence
<220> FEATURE:
<223> OTHER INFORMATION: A synthetic primer

<400> SEQUENCE: 8
acctcgagaa gagagttcca gt                                             22

<210> SEQ ID NO 9
<211> LENGTH: 30
<212> TYPE: DNA
<213> ORGANISM: Artificial Sequence
<220> FEATURE:
<223> OTHER INFORMATION: A synthetic primer

<400> SEQUENCE: 9
gggaattctt agttagaagc gatagtttgc                                     30
```